United States Patent [19]

Poore

[11] Patent Number: 4,802,550
[45] Date of Patent: Feb. 7, 1989

[54] CHRONO-STETHOSCOPE

[76] Inventor: Henry B. Poore, 1003 McFarland St., Norman, Okla. 73069

[21] Appl. No.: 95,828

[22] Filed: Sep. 11, 1987

[51] Int. Cl.⁴ .............................................. A61B 7/02
[52] U.S. Cl. ..................................... 181/131; 368/10
[58] Field of Search ..................... 181/19, 131; 381/67; 368/10, 278, 11; D24/17; 128/677–695, 671, 706, 715

[56] References Cited

U.S. PATENT DOCUMENTS

| D. 285,964 | 9/1986 | Ziebol | D24/17 |
| 735,670 | 8/1903 | Jones | 181/126 |
| 2,829,727 | 4/1958 | Russek | 181/137 |
| 3,247,324 | 4/1966 | Cefaly et al. | 181/131 X |

FOREIGN PATENT DOCUMENTS 818826 10/1951 Fed. Rep. of Germany ...... 181/131

Primary Examiner—B. R. Fuller
Attorney, Agent, or Firm—Laney, Dougherty, Hessin & Beavers

[57] ABSTRACT

A chrono-stethoscope which includes a stethophonic head adapted to detect heartbeats and other bodily sounds. The head is connected to one end of an elongated flexible tubular sound conveyance channel element which carries a detachably mounted timepiece at a location spaced by at least three inches from the stethophonic head. At the other end of the sound channel element, a pair of ear pieces are connected to a main portion of the flexible tubular sound channel element through a bifurcated portion of the channel element which forms a pair of branch tubes. The timepiece is preferably constructed to provide an indication of elapsed seconds of time, and a clip detachably engages it with the tubular sound conveyance channel element.

17 Claims, 2 Drawing Sheets

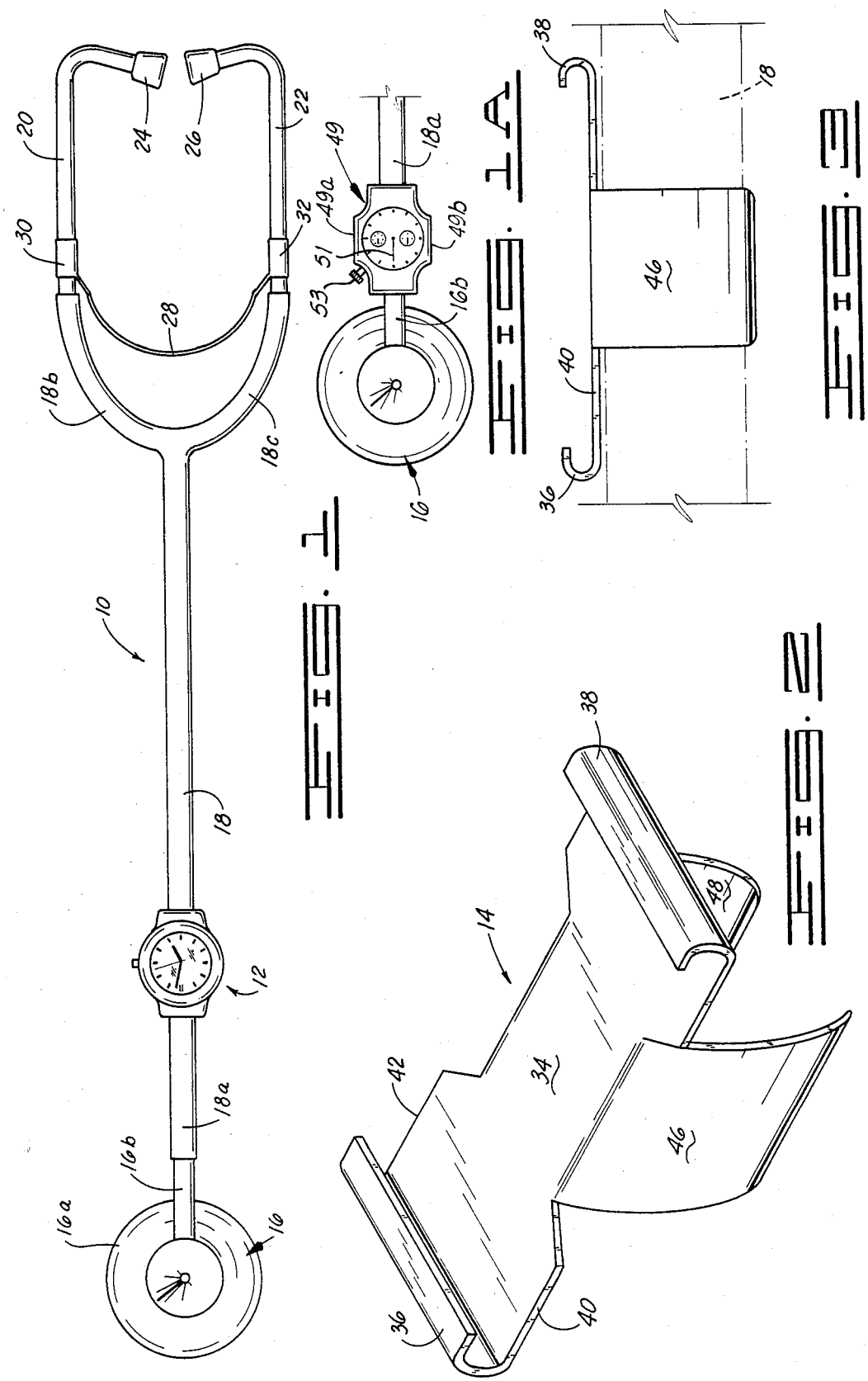

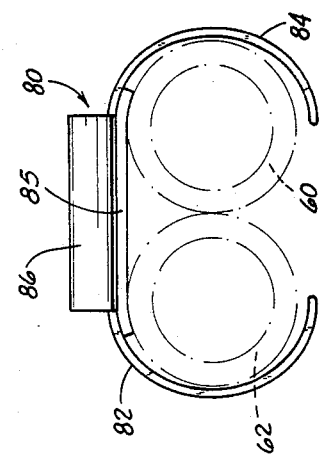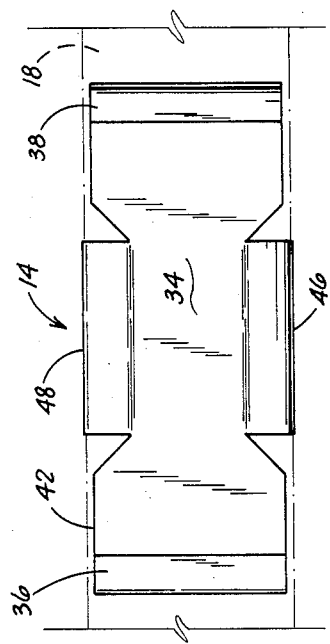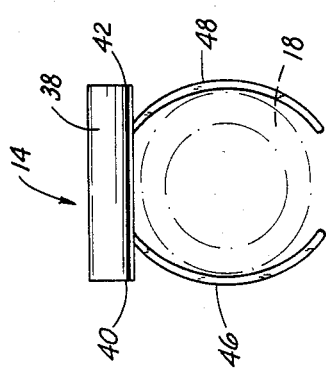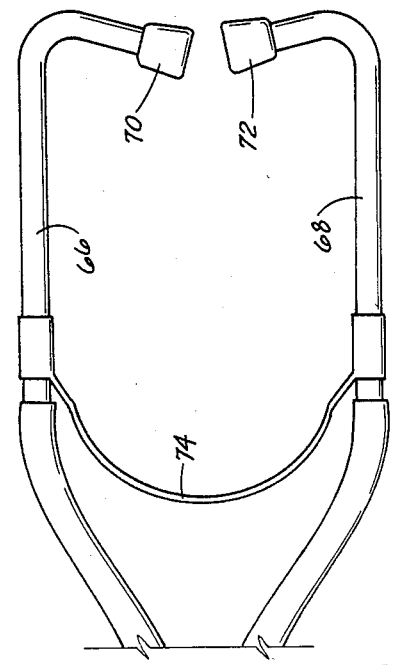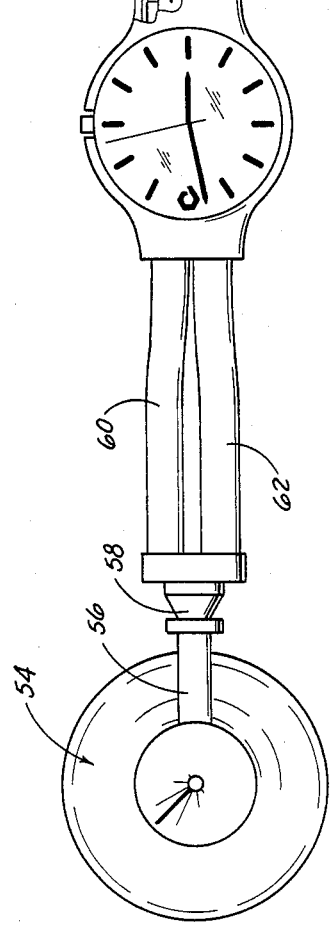

CHRONO-STETHOSCOPE

BACKGROUND OF THE INVENTION

1. Field of the Invention

This invention relates to medical instruments for measuring bodily functions and physiological parameters, and more particularly, to a device for sensing and transmitting sounds originating within the body, and timing a periodicity associated with such sounds.

2. Brief Description of the Prior Art

The stethoscope is a widely used medical instrument which is employed by physicians, nurses, technicians and medical students for conducting sonic physiological diagnostics and testing. As is well known, the stethoscope includes a pickup head, which is placed against the body over the heart or lungs, and one or a pair of flexible, tubular sound conveyance channels. The flexible tubular channels extend from the pickup head to a pair of ear plugs which the nurse, physician or diagnostician wears for the purpose of listening to sounds developed by organs of the body, such as the heart or lungs, which are detectable at the outer surface of the body by the use of the pickup head. Stethoscopes used for the purpose described are of relatively standard construction, and have not undergone significant change for a long period of time.

One of the most important uses of the stethoscope is to listen to the heart sounds of a patient. These sounds are, of course, time-related and normally tend to be rhythmic or, in the case of some types of cardiac anomalies, arhythmic. In order to properly evaluate and diagnose cardiovascular performance, the physician must measure time intervals for the purpose of properly characterizing the heart sounds detected by the use of a stethoscope.

In the past, such timing and rhythmic characterization of stethoscopically-detected sounds originating from the cardiovascular system have been accomplished by the use of a timepiece carried, as is usual and conventional, on the wrist of the physician or the nurse, concurrently with the use of the stethoscope. This, of course, requires that the physician or nurse hold the pickup head of the stethoscope against the body of the patient with one hand, and then turn the other hand and wrist into a position where the timepiece can be observed and the time parameter quantified and synchronized with the cardiovascular sounds.

At this time, the ability of the physician to perform digital manipulations requiring the use of both or even one hand is totally precluded, and either a nurse or third party must perform any needed digital manipulation, or it must wait until the physician has completed his evaluation of the time parameter concurrently with the detection of the bodily-generated sonic emanations. On some occasions and in some situations, a wall clock may be within the view of the physician and may include a second hand which will enable the physician to time a period of listening and heart sound occurrence by observation of such wall clock. On other occasions, however, the position adjacent the patient which must be occupied by the physician does not permit convenient viewing of the wall clock, and it is then essentially useess for the purpose described.

BRIEF DESCRIPTION OF THE PRESENT INVENTION

The present invention offers a chrono-stethoscopic instrument in which the timing function and sonic monitoring function are integrated in a single instrument which is essentially fool proof in its operation, is very simple and easily operated by even relatively unskilled personnel, such as technicians and students, for the first time that it is encountered and used, and which is characterized in having a long and trouble-free operating life.

Broadly described, the chrono-stethoscope of the invention includes a conventional stethoscopic pickup head which can be utilized for sensing sounds emanating from within the body of the patient, an elongated flexible tubular sound conveyance channel element which is connected to the pickup head and conveys the sound therefrom to a pair of ear pieces which in turn carry ear plugs insertable in the ears of the physician. In a preferred embodiment, a spring metal or plastic clip functions to mount a watch or other timepiece, preferably having a second hand, on the tubular sound conveyance channel so that the position of the timepiece therealong can be fixed against inadvertent displacement. The clip grips the tubular sound conveyance channel element in a way, however, such that the physician can manually adjust the position of the clip and timepiece on the stethoscope.

An important object of the invention is to provide a simple structure by which a conventional stethoscope can be quickly and easily modified to secure thereto in a readily accessible, easily observable position, a small, accurate timepiece so that the physician can use this timepiece for timing the frequency of recurrence of body originated sounds detected with the stethoscope.

Another object of the invention is to provide a chrono-stethoscope by which recurrent sonic signals emanating from the body can be timed and characterized in diagnostic examinations and the like carried out by the physician.

Another object of the invention is to provide a stethoscope-timepiece combination which allows a technician, nurse, physical therapist or physician, to manipulate a stethoscope in the usual fashion, and without any need to be distracted, or have his vision diverted from the patient and the stethoscopic pickup head in order to measure or observe a time parameter as he is utilizing the stethoscope.

Another object of the invention is to preclude the need for removing wrist watches prior to scrub up in medical procedures, followed by replacement of the watch thereafter.

Additional objects and advantages will become apparent as the following detailed description of preferred embodiments of the invention is read in conjunction with the accompanying drawings which illustrate such preferred embodiments.

GENERAL DESCRIPTION OF THE DRAWINGS

FIG. 1 is a plan view of one embodiment of the chrono-stethoscope of the invention.

FIG. 1A is a view similar to FIG. 1, but illustrating a modified embodiment of the invention.

FIG. 2 is a perspective view of one embodiment of a clip forming a part of the invention, and utilized for mounting a timepiece on a flexible, tubular sound channel forming a part of a stethoscope.

FIG. 3 is a side elevation view of the clip depicted in FIG. 2. The flexible tubular element of the stethoscope is illustrated in dashed lines.

FIG. 4 is an end elevation view of the clip shown in FIGS. 2 and 3, and illustrating the flexible tubular element of the stethoscope in dashed lines.

FIG. 5 is a plan view of the clip element shown in FIGS. 2-4 and illustrating the clip element as it appears from above, and without the timepiece engaged thereby, at a time when the clip element is engaged with the flexible tubular channel element of the stethoscope.

FIG. 6 is a plan view of a modified embodiment of the chrono-stethoscope of the invention.

FIG. 7 is an end elevation view depicting the appearance of the clip forming a part of the modified chrono-stethoscope of the invention, and illustrating the clip as it would appear as it engaged a pair of flexible tubular elements, as such are utilized in the embodiment of the invention depicted in FIG. 6. These tubular elements are shown in dashed lines in FIG. 7.

DETAILED DESCRIPTION OF PREFERRED EMBODIMENTS OF THE INVENTION

The chrono-stethoscope of the invention may be considered as being made up of three major subassemblies. These are the stethoscope 10, the timepiece 12 and the timepiece mounting clip 14. The stethoscope 10 is of conventional construction and includes a pickup head 16 and at least one flexible tubular sound conveyance sound channel element 18.

The pickup head 16 of the stethoscope 10 is of conventional or typical construction and includes a rubber, plastic or metal cup 16a which can be pressed by the physician against the chest or other portion of the body of the patient for the purpose of listening to internal, physiologically originated sounds. The rigid tubular neck portion 16b of the pickup head 16 is telescopingly press-fit into an open end 18a of a flexible, tubular sound conveyance channel element 18. When the physician uses the stethoscope in typical fashion, it is usual to grip the stethoscope by holding a tubular rigid neck portion 16b of the pickup head 16 and the adjacent flexible tubular sound channel element between the thumb and one or two fingers.

The elongated flexible tubular sound conveyance channel element 18 is constructed of rubber or plastic and is typically from about 14 inches to about 18 inches in length—a length which is generally adequate to permit the physician or nurse to stand a comfortable distance from the patient while conducting the stethoscopic examination. At its end opposite the end 18a into which the neck 16b of the pickup head 16 is inserted, the elongated tubular sound conveyance channel element 18 is bifurcated, and thus includes a pair of substantially identical branch tubes 18b and 18c. The branch tubes 18b and 18c form a Y-shaped structure with the principal portion of the elongated flexible tubular sound conveyance channel element 18.

A pair of rigid tubular L-shaped ear pieces 20 and 22 are connected to the two tubular branches 18b and 18c by telescopingly pressing the ends of the rigid ear pieces into the open ends of the respective tubular branches. The rigid L-shaped ear pieces 20 and 22 are rotated so that the angled end portions thereof are angled toward each other as illustrated in FIG. 1. Each of the ear pieces 20 and 22 carries a relatively soft resilient ear plug. These ear plugs are designated by reference numerals 24 and 26.

It is, of course, essential to retain the rigid ear pieces 20 and 22 in a position such that ear plugs 24 and 26 will remain in the ears of the physician or nurse as the stethoscope is used. For this purpose, a U-shaped spring element 28 is connected between a pair of sleeves 30 and 32. The sleeves 30 and 32 surround and engage the rigid tubular elements 20 and 22 at a location near the point where they enter the tubular branches 18b and 18c. The spring element 28 is bowed away from the ends of the ear pieces 20 and 22 which carry the ear plugs 24 and 26, and is spaced a sufficient distant from the ear plugs that the physician can place the plugs in his ears as the spring element 28 passes across the forward side of his neck or in front of his face.

The stethoscope 10 as it has been described, and as it is illustrated in FIG. 1 of the drawings, is a typical stethoscope construction, and no part of the present invention resides in the construction of the stethoscope, per se. It will be understood that other models and types of stethoscopes may vary slightly in structural detail without departure from the basic overall configuration, and the inclusion of basic subassemblies which are essential to the proper functioning and utilization of the stethoscope. The manner in which all stethoscopes are constructed, so far as I am aware, is generally important to an understanding and appreciation of the present invention, however. This is because certain dimensions and certain characteristics of flexibility, as well as the mode of stethoscopic utilization, all are important to the usefulness of the present invention, and the facility with which it can be employed effectively by a physician without interferring with the normal functions and utilization of the stethoscope.

The clip 14 by which the timepiece 12 is detachably secured at a critical position upon, and in a critical way to, the stethoscope 10 is illustrated in FIG. 2. The clip 14 can conveniently, and in a preferred embodiment, be stamped from a flat sheet of metal and bent to the configuration illustrated in FIG. 2. In this preferred embodiment, the clip 14 includes a flat central base plate 34. The base plate 34 is reversely bent or turned over at its opposite ends so as to provide a pair of opposed pin-engaging flanges 36 and 38. The base plate 34 includes a pair of parallel side edges 40 and 42. Into each of the side edges 40 and 42 are cut a pair of convergent inwardly directed cuts or notches to facilitate the bending downwardly, out of the plane of the base plate 34, of a pair of tubeengaging, semi-cylindrical band elements 46 and 48. In the illustrated embodiment of the clip 14, the band elements 46 and 48 are opposed and lie generally upon the outer periphery of a figure of revolution.

The clip 14 can also be molded of plastic, and in such uses, it is possible to make the clip a part of the flexible sound conveyance channel element. The manner in which the clip 14 is secured upon the flexible elongated tubular sound conveyance channel element 18 of the stethoscope 10 is depicted in FIGS. 3, 4 and 5. As reference is made to these figures, it will be perceived that the band elements 46 and 48 are curved around the outer periphery of the flexible tubular sound conveyance channel element 18 so as to frictionally engage the outer peripheral surface of this generally cylindrical flexible tubular element. At the same time, the base plate 34 bears flatly against the outer periphery of the tubular sound conveyance channel element 18 and extends substantially parallel to the longitudinal axis of this elongated tubular element.

The manner in which the clip 14 is utilized for retaining the watch or timepiece on the flexible tubular sound conveyance channel element 18 is best illustrated in FIGS. 4 and 5 of the drawings. In typical wrist watch construction, the watch will be provided with a pair of band pins 50 at its opposite sides. One of the pins will normally extend across that side of the watch which carries the indicia "12", and the other will extend parallel to the first pin and on the opposite side of the watch adjacent the location of the indicia "6".

The pins 50 are dimensioned to permit them to be engaged by the two opposed, parallel, turned over pin-engaging flanges 36 and 38 at opposite sides of the base plate 34. In this way the timepiece 12 is held firmly so that its back bears flatly against the base plate 34, and the pin-engaging flanges 36 and 38 prevent it from shifting from the position illustrated. It should be pointed out that in one embodiment of the invention, there is sufficient spring flexibility and resiliency in the base plate 34 and in the opposed pin-engaging flanges 36 and 38 that these elements can be resiliently bent out of the illustrated positions sufficiently to permit the watch to be snapped in between the two pin-engaging flanges. In yet other, less preferred embodiments of the invention, the base plate 34 and the back plate of the watch may be integrated and made a single unit, in which case there is, of course, no necessity for the pin-engaging flanges.

It will be noted that the orientation of the clip 14 on the flexible tubular sound conveyance channel element 18 is such that the pin-engaging flanges 36 and 38 always extend substantially transversely across (normal to) the longitudinal axis of the sound conveyance channel element. This positioning of the flanges 36 and 38 assures that the watch or timepiece will be oriented along the tubular sound conveyance channel element 18 so that when the hour and minute hands show 6:00 o'clock, the hands are extending parallel to, and in alignment with, the longitudinal axis of the tubular sound conveyance channel element 18. This position greatly facilitates the ease with which a physician or nurse can use the chrono-stethoscope, because with the timepiece so oriented, it is very easy for the physician to read the time shown thereon at the same time that he has placed the pickup head 16 against the body of the patient.

At some times, it may be desirable to remove the timepiece from the tubular sound conveyance channel element 18 of the chrono-stethoscope 10. This can be easily and quickly accomplished by simply springing apart the tube-engaging semicylindrical band elements 46 and 48. The spring metal construction of the clip 14 is such that springing these band elements 46 and 48 apart to facilitate removal of the timepiece from the stethoscope does not damage or significantly weaken the clip 14 so as to prevent it from being re-utilized to re-attach the time piece 12 to the stethoscope 10 at such time as the assembling of the chrono-stethoscope for subsequent utilization is required.

It should be pointed out that the tube-engaging, semicylindrical band elements 46 and 48 frictionally grip or engage the outer periphery of the flexible tubular sound conveyance channel element 18 with a limited constricting force. This engagement is only sufficient to prevent the clip 14 and the timepiece 12 carried thereon from sliding along the tubular sound conveyance channel element 18 unless it is deliberately and forcefully manually pushed along the channel element. The physician, nurse or technician is thus able to adjust the position of the timepiece on the stethoscope.

In the most prevalent and widespread mode of usage of the chrono-stethoscope, the clip 14 and the timepiece that it carries will be positioned at least three and preferably five inches from the pickup head 16. This will allow adequate space for the physician to grip the sound conveyance channel element 18 of the stethoscope 10 at a location where the pickup head 16 can be easily manipulated and placed on the body precisely where the physician desires without any interference from the clip or the timepiece. It will also permit the timepiece 12 to be clear of the physician's hand used to grip and manipulate the chrono-stethoscope, so that the movement of a timepiece second hand can be observed, and the time on the timepiece 12 can be quickly and easily read. In this regard, it is again pointed out that the spacial orientation of the timepiece 12 relative to the pickup head 12 and to the tubular sound conveyance channel element 18 is such that as the pickup head is placed against the body, the watch or timepiece will almost invariably be exposed to the clear visual observation by the physician or nurse.

This invention, in eliminating the need to use a wrist watch for timing the recurrence of bodily sounds, also eliminates the need for removing a wrist watch when scrubbing prior to surgical procedures, and alleviates any concern about the wrist watch being obscured or hidden by shirt sleeve or suit sleeve during routine stethoscopic examinations.

FIG. 1A of the drawings illustrates the construction of a particular embodiment of the invention which has special utility. As here shown, a different type of timepiece, denominated by reference numeral 49, is shown at a specific location which is relatively close to the pickup head 16. The timepiece 49 is here firmly clamped about the tubular rigid neck 16b and the end portion 18a of the sound conveyance channel element 18. It will be noted that the timepiece 49 has a pair of opposed, relatively flat sides 49a and 49b which extend parallel to each other and parallel to the longitudinal axis of the channel 18, and to the axis of the tubular rigid neck 16b. It will further be noted that in this particular form of the invention, the timepiece 12 has a protruding sweep second hand stop tab 53 which can be used to start and stop a sweep second hand 51 carried by the timepiece 49.

In the utilization of this particular form of the invention, the timepiece 49 itself affords surfaces 49a and 49b for gripping the instrument so as to position the pickup head 16 against the point on the body where the physician or nurse desires it to be located as he listens for bodily sounds. In doing this, the physician will place the thumb along one flat surface 49a of the timepiece 49, and the pointer and index fingers along the second flat surface 49b of the time piece. If the physician then desires to time a particular period, or the periodicity of cyclically occurring sounds within the body, this can be easily done by simply depressing the sweep second hand stop tab 53 to start the second hand, and then depressing it again to stop the second hand after an elapsed time interval.

Another modified embodiment of the invention is illustrated in FIGS. 6 and 7 of the drawings. Here, a different type of stethoscope is utilized in the construction of the chrono-stethoscope of the invention. The stethoscope shown in FIG. 6 includes a pickup head 54 which has a rigid neck 56 connected thereto and a header 58 connected between the rigid neck 56 and a pair of elongated flexible, resilient tubular sound conveyance channel elements 60 and 62. The sound conveyance channel elements 60 and 62 are similar to the sound conveyance channel element 18 previously described, except that one end of the elements 60 and 62 is joined to the header 58.

At its other end, each of the sound conveyance channel elements 60 and 62 is joined to an open end of one of a pair of rigid L-shaped ear pieces 66 and 68. The rigid L-shaped ear pieces 66 and 68 can be identical to the rigid L-shaped ear pieces 20 and 22 which have been described in referring to FIG. 1 of the drawings. The rigid L-shaped ear pieces 66 and 68 carry a pair of ear plugs 70 and 72, as previously described. The rigid ear pieces are positioned so that the ear plugs 70 and 72 will extend into the ears of the physician and remain there by reason of the bias exerted by the U-shaped spring element 74 as has previously been described.

In the embodiment of the chrono-stethoscope shown in FIGS. 6 and 7, a spring metal clip 80 is provided which is similar in its functional characteristics to the spring metal clip 14 hereinbefore described. The base plate of this clip 80 will generally, however, be slightly wider than the base plate 34 of the clip 14 earlier described, since the clip must function to attach a timepiece or watch to the dual sound conveyance channel elements 60 and 62. In other words, the clip 80 must span across two of these flexible tubular sound conveyance channel elements as shown in FIG. 7. In order to permit both of the tubular sound conveyance channel elements 60 and 62 to be engaged by the clip 80, the clip has a pair of opposed arcuate tube-engaging semi-cylindrical band elements 82 and 84 as shown in FIG. 7. The clip 80 also carries a pair of opposed, parallel, turned over or reverse-bent, pin-engaging flanges 86 similar to those carried by the clip 14 of the first described embodiment. These flanges function in the same way as has been previously described for the purpose of engaging the pair of pins which is conventionally provided on a watch or timepiece. Finally, in the embodiment of the invention shown in FIG. 7, a flat plate 85 of sound barrier materials is interposed between the clip 80 and the tubular elements 60 and 62 to assure that any sound from the watch is not picked up.

In the use of the chrono-stethoscope of the invention, a physician, nurse, student or technician employs the stethoscope substantially as it has been employed in the past, i.e., the pickup head is placed against the body of the patient at a location where it is desired to pick up body sounds originated within the body, and monitor these sounds. At the time the physician uses the pickup head for this purpose, he does so without obscuring or blocking his vision so that the timepiece cannot be seen. Rather, the timepiece always remains in a clearly readable position, an in observing the position where the pickup head is placed, the physician will necessarily also be positioned to observe where the timepiece is located and what time is indicated on its face.

If it is desirable during the monitoring of the sounds developed within the body to time the frequency of occurrence of certain sounds or the rate at which certain sounds, such as heart beats, recur, this can be accomplished in a facile fashion by the use of the timepiece carried on the sound conveyance channel element(s) of the stethoscope. The physician does not need to move his left arm or right arm into a position in front of his eyes in order to read the time from a wrist watch. Neither need he look up away from the patient toward a wall clock in order to be apprised of the time, or the rate of passage of time. In many crucial situations, this is an important consideration because the physician is not in any way distracted by the timepiece, considering where it is located, but, in the alternative, neither is he distracted from the work at hand by the need to ascertain the passing of a given span of time by looking away from the patient toward a remotely positioned timepiece.

Although certain preferred embodiments of the invention have been herein described in order to afford an enlightened understanding of the invention, and to allow its principles to be utilized, it should be understood that various changes and innovations in the described structures can be effected without departure from the basic principles thereof, except as the same may be necessarily limited by the appended claims or reasonable equivalents thereof.

What I claim is:

1. A chrono-stethoscopic device comprising:
   a stethoscope including:
      a pickup head;
      an elongated, flexible, tubular sound conveyance channel element having a first end connected to said pickup head, and having a second end; and
      a pair of ear pieces connected to said second end;
   a timepiece; and
   means for detachably and adjustably movably securing said timepiece to said elongated flexible tubular sound conveyance channel element at a position which is located between said pickup head and said ear pieces and not more than ten inches from said pickup head.

2. A chrono-stethoscopic device as defined in claim 1 wherein said securing means comprises a clip having turned over, reverse bent, parallel pin-engaging flanges engaging said time-piece, and further having opposed band elements which are curved and are in engagement with said flexible tubualr channel element.

3. A chrono-stethoscopic device as defined in claim 2 wherein said clip is formed from a single flat rectangular spring metal piece.

4. A chrono-stethoscopic device as defined in claim 1 and further characterized as including a pair of ear plugs connected to said ear pieces at a location remote from the ends of said ear pieces connected to said channel element.

5. A chrono-stethoscopic device as defined in claim 1 and further characterized as including a flexible, resilient bifurcated tubular section connected between said second end of said channel element and said pair of ear pieces.

6. A chrono-stethoscopic device as defined in claim 2 wherein said timepiece is further characterized as including a pair of parallel pins snap engaged by said pin-engaging flanges 7. A chrono-stethoscopic device comprising:
   a stethoscope including:
      a pickup head;
      an elongated, flexible, resilient tubular means having a first end portion connected to said pickup head, and having a second end portion; and
      a pair of spaced ear plugs movably connected to said second end portion; and
   timepiece means mounted on said stethoscope for manual sliding movement along said tubular means toward and away from said pickup head, and gripping and engaging said tubular means to resist inadvertent axial displacement therealong.

8. A chrono-stethoscopic device as defined in claim 7 wherein said timepiece means includes a timepiece and clip means secured to said timepiece and slidingly clasping said tubular means with a frictional engagement adequate to maintain said timepiece means in a selected location on said tubular means.

9. A chrono-stethoscopic device as defined in claim 7 wherein said timepiece means is positioned immediately adjacent said pickup head, and said timepiece means includes a timepiece having a pair of lateral, opposed, gripping surfaces to facilitate gripping of the timepiece by the physician to manipulate the pickup head to a desired position adjacent the body, and wherein said timepiece further includes a sweep second hand actuating tab protruding from said timepiece at a location adjacent said gripping surfaces to facilitate stop watch utilization of the second hand of said timepiece by the physician.

10. A chrono-stethoscopic device as defined in claim 7 and further characterized as including means resiliently interconnecting said spaced ear plugs to retain said ear plugs in an "at rest", unbiased position in which they will fit and stay within the ears of the physician when the chrono-stethoscopic device is in use.

11. A chrono-stethoscopic device as defined in claim 8 wherein said clip means comprises:
reverse turned flange means engaging said timepiece means; and
a pair of arcuate, rigid resilient band elements engaging said elongated, flexible, resilient tubular means.

12. A chrono-stethoscopic comprising:
a pickup head;
at least one ear plug;
means for transmitting sound from the pickup head to each ear plug; and
timepiece means detachably and movably mounted on said transmitting means for movement from a first position relatively near said pickup head to a second position relatively more remote from said pickup head by sliding movement along said sound transmitting means.

13. A chrono-stethoscopic device comprising:
a stethoscope including:
a pickup head;
an elongated, flexible, tubular sound conveyance channel element having a first end connected to said pickup head, and having a second end; and
a pair of ear pieces connected to said second end;
a timepiece having hour and minute hands; and
a clip for securing said timepiece to said tubular sound conveyance channel element, said clip comprising:
turned over, reverse bent, parallel, pin-engaging flanges extending transversely across a longitudinal axis of said elongated, flexible, tubular sound conveyance channel element and engaging said time piece; and
opposed, curved band elements in engagement with said flexible tubular sound conveyance channel element so that said timepiece is oriented along said channel element so that when the hour and minute hand thereof point to six o,-clock, the hand of the timepiece are in alignment with, and extend parallel to, a longitudinal axis of said elongated flexible tubular sound conveyance channel element.

14. A chrono-stethoscopic device comprising:
a stethoscope including:
a pickup head;
an elongated, flexible, tubular sound conveyance channel element having a first end connected to said pickup head, and having a second end; and
a pair of ear pieces connected to said second end;
a timpiece; and
a clip for securing said timepiece to said stethoscope, said clip including band means grippingly and frictionally engaging an outer periphery of said flexible tubular sound conveyance channel element with a frictional engagement preventing inadvertent displacement of said timepiece in a longitudinal direction along said channel element, while facilitating a manual, selective positioning of said timepiece along a length of said channel element by sliding displacement of the timepiece therealong.

15. A chrono-stethoscopic device comprising:
a stethoscope including:
a pickup head;
an elongated flexible tubular sound conveyance channel element having a first end connected to said pickup head, and havinq a second end; and
a pair of ear pieces connected to said second end;
a timepiece;
means for slidably securing said timepiece to said flexible tubular sound conveyance channel element; and
a sound barrier material positioned between said time-piece and said flexible tubular sound conveyance channel element.

16. A chrono-stethoscopic device comprising:
a stethoscope including:
a pickup head;
an elongated flexible, tubular sound conveyance channel element having a first end connected to said pickup head, and having a second end; and
a pair of ear pieces connected to said second end;
a timepiece; and
securing means for securing the timepiece to said stethoscope, said securing means including:
a clip having turned over, reverse bent, parallel pin-engaging flanges engaging said timepiece and extending transversely across a longitudinal axis of said elongated flexible tubular sound conveyance channel element; and
opposed, curved band elements in engagement with said flexible, tubular channel elements.

17. A chrono-stethoscopic device comprising:
a stethoscope including:
a pickup head;
an elongated, flexible, resilient tubular means having a first end portion connected to said pickup head, and having a second end portion; and
a pair of spaced ear plugs movably connected to said second end portion; and
a timepiece mounted on said stethoscope immediately adjacent said pickup head, said timepiece having a pair of lateral, opposed, gripping surfaces to facilitate gripping of the timepiece by a physician to manipulate the pickup head to a desired position adjacent a body, and wherein said timepiece further includes a sweep second hand actuating tab protruding from said timepiece at a location adjacent said gripping surfaces to facilitate stop watch utilization of the second hand of said timepiece by the physician.

* * * * *

UNITED STATES PATENT AND TRADEMARK OFFICE
CERTIFICATE OF CORRECTION

PATENT NO. : 4,802,550
DATED : February 7, 1989
INVENTOR(S) : Henry B. Poore

It is certified that error appears in the above-identified patent and that said Letters Patent is hereby corrected as shown below:

<u>In the Specification:</u>
In Column 1, line 68, delete "useess" and insert -useless-.
<u>In the Claims:</u>
In Column 8, line 38, delete "time-piece" and insert -timepiece-.
In Column 8, line 40, delete "tubualr" and insert -tubular-.
In Column 8, line 57, after the word "flanges" insert -to facilitate quick detachment of said timepiece from said clip.-
In Column 9, line 64, delete "hand" and insert -hands-.
In Column 9, line 64, delete "o," and insert -o'-.
In Column 9, line 65, delete "hand" and insert -hands-.

Signed and Sealed this

Fourth Day of July, 1989

*Attest:*

DONALD J. QUIGG

*Attesting Officer*  Commissioner of Patents and Trademarks